United States Patent [19]

Hedrick

[11] Patent Number: 4,996,656

[45] Date of Patent: Feb. 26, 1991

[54] DENSITOMETER WITH REMOTELY DISPOSED CONTROL ELECTRONICS

[75] Inventor: Geoffrey S. M. Hedrick, Malvern, Pa.

[73] Assignee: Innovative Solutions & Support, Incorporated, Malvern, Pa.

[21] Appl. No.: 241,017

[22] Filed: Sep. 2, 1988

[51] Int. Cl.[5] .............................................. G01N 9/00
[52] U.S. Cl. .................................. 364/558; 73/32 A; 364/509
[58] Field of Search ................... 364/558, 424.01, 480, 364/484, 506, 508, 509; 73/32 R, 32 A, 54, 579

[56] References Cited

U.S. PATENT DOCUMENTS

| | | | |
|---|---|---|---|
| 3,795,136 | 3/1974 | Schlatter | 73/32 A |
| 3,878,374 | 4/1975 | Schlatter | 364/509 X |
| 4,037,459 | 7/1977 | Schlatter | 73/32 A |
| 4,240,285 | 12/1980 | Langdon | 73/32 A |
| 4,546,641 | 10/1985 | Nguyen | 73/32 A |
| 4,783,987 | 11/1988 | Hager et al. | 73/579 X |
| 4,788,466 | 11/1988 | Paul et al. | 73/32 A X |
| 4,802,360 | 2/1989 | Maier | 73/32 A |
| 4,815,323 | 3/1989 | Ellinger et al. | 73/32 A |
| 4,838,084 | 6/1989 | Leopold | 73/32 A |
| 4,848,139 | 7/1989 | Blake-Coleman et al. | 73/32 A X |

Primary Examiner—Joseph L. Dixon
Attorney, Agent, or Firm—Cohen, Pontani & Lieberman

[57] ABSTRACT

A fluid density measuring device or densitometer computes, electronically, the density of a fluid by measuring the resonant frequency of an excitation signal provided to a density transducer (11) immersed in the fluid. The frequency at which resonance occurs in the circuit (13, 15, 17, 21, 23, 25, 29, 31, 37, 41) will vary according to the density of the fluid, and this information is used by measuring electronics (31, 37, 41, 43), including a programmed microprocessor (43), to calculate the density of the fluid. The output of the microprocessor (43) may be a display of fluid density information or may be transmitted to a fuel gauge.

9 Claims, 8 Drawing Sheets

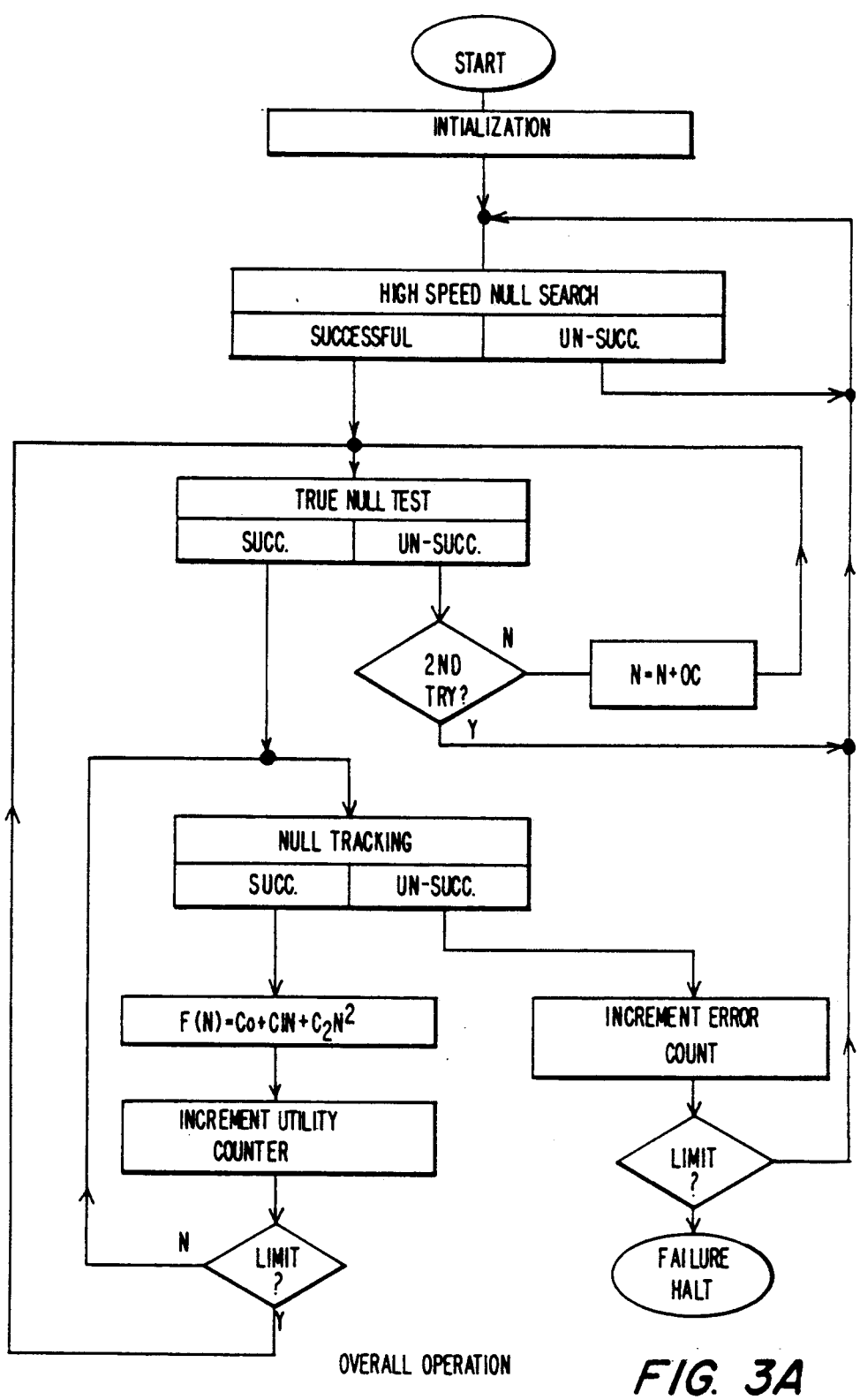
FIG. 3A — OVERALL OPERATION

HIGH SPEED NULL SEARCH SUB-ROUTINE

TRUE NULL TEST SUB-ROUTINE

NULL TRACKING SUB-ROUTINE

DENSITOMETER WITH REMOTELY DISPOSED CONTROL ELECTRONICS

FIELD OF THE INVENTION

The present invention relates to a device for measuring the density of fluid. More particularly, the present invention relates to an electronic densitometer, the output of which may either be displayed or transmitted to a fuel gauge for measuring fluid volume in a tank, such as an aircraft fuel tank.

BACKGROUND OF THE INVENTION

Devices for measuring fluid density are known. Such devices typically use a density transducer comprising a transducer head containing a vibrating cylinder. The cylinder is caused to vibrate by a magnetic field generated by an alternating current in a coil surrounding the cylinder. The density transducer cylinder, immersed in the fluid to be measured, will have a resonant frequency of vibration that is dependent upon the density of the surrounding fluid. Measurement of this resonant frequency by electronic circuitry permits calculation of the fluid density. An example of a density transducer is the Avionic Liquid Density Transducer, 7824 Series, manufactured by Solartron, a division of Schlumberger Electronics (UK) Ltd.

The measuring electronics for this device typically have been required to be physically located near (e.g. within 2 to 3 meters of) the density transducer itself. A common arrangement has been to mount the electronics in a module that is located directly opposite the transducer head, on the outside of the fuel tank. The reason for such close mounting has been that, because of impedance, the resonance of the circuit is affected by the length of the electrical leads running to the transducer, and the electronics typically cannot adequately compensate for such effect on resonance. Without proper compensation, an inaccurate density reading will be produced.

The disadvantages of such an approach are apparent, particularly in harsh environments such as those encountered by aircraft fuel tanks which are often subject to vibration and temperature and pressure extremes. Locating the measuring electronics on or near the fuel tank not only may be physically awkward from a design, engineering or space standpoint, but also increases the risk of malfunction in the electronics due to the harsh environment, and may render the electronics difficult to repair because of inaccessability.

SUMMARY OF THE INVENTION

The problems noted above are solved with the present invention. Broadly, the invention comprises:
a density transducer having input means for receiving an excitation signal and output means for generating a pick-up signal responsive to the excitation signal and to the density of a fluid in which the density transducer is immersed; and
excitation and measurement electronics coupled to the density transducer, comprising;
means for producing an excitation signal of variable frequency for input to the density transducer;
means for varying the frequency of the excitation signal in response to a variation in the phase relationship of the excitation signal and the pick-up signal so as to maintain resonance between the excitation signal and the pick-up signal; and
means for detecting the phase relationship between the excitation signal and the pick-up signal and for producing an output signal corresponding to the fluid density upon detection of resonance;
the densitometer being capable of accurately measuring fluid density despite a wide separation between the density transducer and the excitation and measurement electronics.

The present invention permits the measurement of the density of a wide range of fluids as, for example, in the range of fluid densities between 5 lbs/gal and 7.5 lbs/gal.

The electronics can be applied to other transducers (e.g. air pressure) whose method of measurement requires an excitation signal to find a resonance point. Modification of certain components (i.e. oscillator, dividers) may be required depending upon the transducer's characteristics. It finds particular application, for example, in the measurement of liquid fuel such as aviation fuel. A density transducer is immersed in the fluid and provides a electrical output (the transducer pick-up signal) in response to an excitation signal. The pick-up signal is then electronically compared to the excitation signal, and when a coincidence between the two signals of 90 degrees phase shift is achieved, this signifies that resonance in the transducer has been achieved, and a microprocessor is then caused to enter a subroutine to generate an output display of the fluid density which is a function of the resonant frequency. The microprocessor preferably also transmits the density information output signal to a fuel gauge.

The density transducer in the fluid is maintained in a resonant mode at all times via a feedback loop. Different densities of the fluid will cause resonance to occur at different frequencies of the excitation signal entering the density transducer. The period of the excitation signal at which resonance occurs is used by the microprocessor to calculate, via a mathematical polynomial, the density of the fluid.

The measuring and excitation electronics are not required to be physically located adjacent to or near the density transducer but may, instead, be located hundreds of feet away. The effect of the long runs of electrical leads on the resonance of the circuit is fully compensated for by the present invention.

Other objects and features of the present invention will become apparent from the following detailed description considered in conjunction with the accompanying drawings. It is to be understood, however, that the drawings are designed for purposes of illustration only and not as a definition of the limits of the invention for which reference should be made to the appended claims.

BRIEF DESCRIPTION OF THE DRAWINGS

In the drawings, wherein similar reference characters denote similar elements throughout the several views:

FIGS. 3A, 3B, 3C, 3D and 3E are flow charts of a software implementation of the embodiment of the invention depicted in FIG. 2B.

DETAILED DESCRIPTION OF THE PREFERRED EMBODIMENTS

Figure 1:
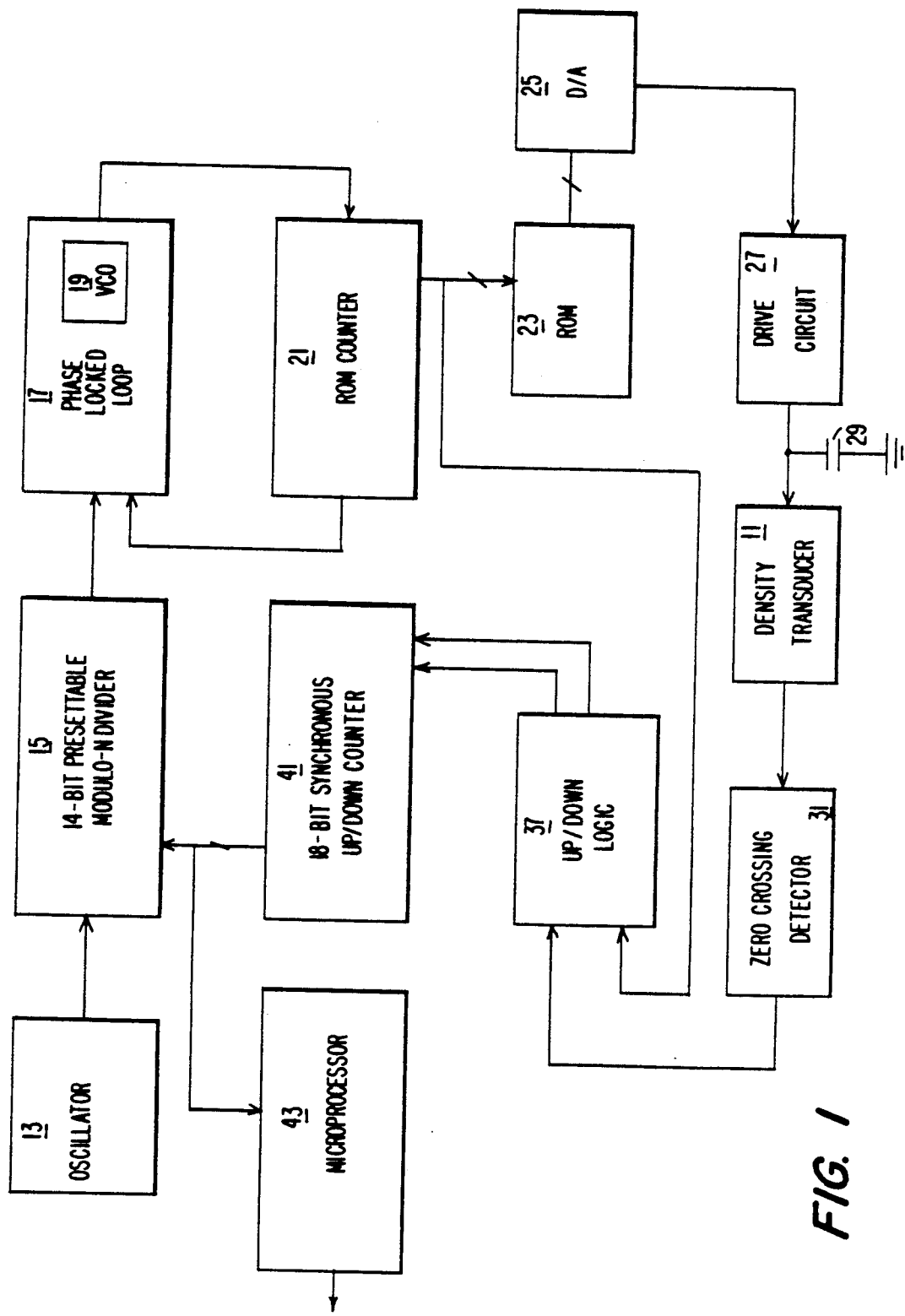
FIG. 1 is a functional block diagram of a first embodiment of the present invention.

Turning now to the first disclosed embodiment of the invention as illustrated in FIG. 1, a density transducer 11 is provided for measuring the density of a fluid, such as aircraft fuel. Density transducer 11 may, for example, comprise an avionic liquid density transducer of the vibrating cylinder type, such as the 7824 Series manufactured by Solartron, a division of Schlumberger Electronics (UK) Ltd. Such a transducer is designed to be immersed in the fluid to be measured and is designed to provide a continuous density measurement upon connection to electronic circuitry, such as that of the present invention as described below, which provides excitation and measurement (read-out) functions.

Applied to the input of the transducer 11 is a cosine wave analog excitation signal generated by the combination of an oscillator 13, a 14-bit presettable modulo-N divider 15, a phase locked loop 17, a read-only memory (ROM) counter 21, a ROM 23, a digital-to-analog (D/A) converter 25 and a drive circuit 27, all as shown in FIG. 1.

Oscillator 13, which acts as a clock, generates a pulse train for input to the 14-bit presettable modulo-N divider 15. Divider 15, in turn, is coupled to phase locked loop 17. Oscillator 13 is of conventional design and may, for example, comprise an integrated circuit such as a National model 74HCO4. Divider 15 is also conventional and may comprise four National integrated circuits, model 74HC193, connected in series. Phase locked loop 17 may also comprise a conventional circuit, such as a Motorola phase detector, model MC4044, coupled to a Motorola voltage controlled oscillator (VCO), model MC4024.

In a preferred embodiment, the frequency of the pulse train from oscillator 13 to divider 15 is on the order of 3 MHz. The frequency of the divider output signal provided by divider 15 to loop 17 is determined by the preset value of the modulus (divisor) of divider 15 and is variable. The divisor may, for example, be in the range of approximately 12,288 to 16,383 for an aircraft fuel application, and the divider output signal frequency may thus be in the range of approximately 244 Hz to 183 Hz for this application.

In a feature of the present invention, phase locked loop 17, which contains VCO 19, is coupled to ROM counter 21 in such a way as to form a closed loop, as shown in FIG. 1. VCO 19 is maintained at a frequency 128 times the necessary excitation frequency (discussed below) of density transducer 11. In a preferred embodiment, ROM counter 21 is a 13-stage synchronous counter constructed from, for example, four National integrated circuits, models 74HC193, coupled in series.

The output from phase locked loop 17, a clock signal whose frequency may be on the order of 1.5 MHz to 2 MHz, enters the ROM counter 21, which divides the clock signal down. One output of counter 21 is fed back to the input of loop 17 for comparison purposes, to provide stabilization of the clock signal frequency and to serve as feedback in the phase locked loop circuit.

ROM counter 21 also provides a digital reference signal at another output, which signal is fed to ROM 23 and to up/down logic circuit 37. The reference signal data path from ROM counter 21 to ROM 23 may be a 7-bit parallel path or bus, and the reference signal data path to the up/down logic circuit 37 may be a one-bit path. ROM 23 may, for example, comprise a National integrated circuit, model 2716.

In an additional feature of the invention, ROM 23 is programmed with amplitude information used for generating a cosine wave to be generated at 128 equally spaced portions of the wave. The lower 7-bits of the ROM counter 21 are used to address the 128 samples of the cosine wave contained within the ROM. ROM counter 21 counts from zero, up to 127, and then restarts the cycle, and thereby steps through the addresses of ROM 23 in a sequential manner. The rate at which the ROM counter is incremated is controlled by the frequency of VCO 19. For every cycle through the ROM counter 21, sixty-four cosine wave cycles are generated. Thus, in the preferred embodiment, this provides an average of sixty-four cosine waves for each cycle of the divider 15.

The output of ROM 23 is connected to digital-to-analog (D/A) converter 25 via an 8-bit bus, as shown in FIG. 1. D/A converter 25 may, for example, comprise a conventional integrated circuit, such as National model DAC-08. The data from the ROM 23 is presented to the converter 25 when the circuit sequences through the addresses at which the data resides in the ROM. The rate at which the ROM is addressed determines the frequency of the generated waveforms.

The resulting cosine wave (which is considered to be an analog reference signal) generated at the output of the D/A converter 25 is then sent to drive circuit 27 for amplification, and is then used to provide an excitation signal for density transducer 11. Drive circuit 27 also provides current limiting and DC decoupling at the transducer drive coil. One terminal of a capacitor 29 is connected to the signal path between the transducer 11 and drive circuit 27 in order to provide resonance at the transducer coil and to minimize the current in the interconnecting cables. The other terminal of capacitor 29 is grounded. An important feature of the invention is that the cosine wave excitation signal at the output of drive circuit 27 may be sent over to a considerable distance to the density transducer 11. The transducer may, for example, be located in a remote location up to 300 feet from drive circuit 27 and the other electronic components.

The output of density transducer 11, known as the pick-up signal, is returned to the measuring electronics for measurement of fluid density as follows. The output lead from the transducer is attached to zero crossing detector 31, to which the pick-up signal is applied. When the transducer 11 is in resonance, the output of zero crossing detector 31 is a logical 0 or a pulse train that is 90 degrees out of phase with, specifically lagging, the excitation signal entering transducer 11. Zero crossing detector 31 may, for example, comprise a high gain amplifier such as Texas Instruments IC model TL084 connected in series with a Schmidt trigger, such as National IC model 74C914.

In another feature of the invention, the signals from the zero crossing detector and the ROM counter 21 are input to up/down logic 37, as shown in FIG. 1. Up/down logic 37 may, for example, comprise a D-type flip flop, such as National IC model 74HC00. The up/down logic compares the signal from zero crossing detector 31 with the reference signal, shown in FIG. 1 as coming from ROM counter 21, and provides an output (either "up" or "down") based upon the phase relationship of these inputs. The reference signal input to the up/down logic 37 is derived from the most significant address bit of the ROM 23. This address bit is at the same frequency as the excitation signal to the density transducer 11. ROM 23 is programmed so that the most significant address bit changes state at the zero and 180 degree points of the generated cosine wave. This bit is therefore in phase with the pick-up signal at the output of transducer 11 and 90 degrees out of phase with the reference signal when the transducer is in resonance. Small changes in the excitation frequency will result in varying phase relationships with the pick-up return. The sample circuitry searches for and locks on a 90 degree shift.

Thus, the logic level of the signal at the output of zero crossing detector 31, which is used as one of the inputs to up/down logic circuit 37, is applied to a D-type flip flop within the up/down logic. The D-type flip flop is clocked on the leading edge of the most significant address bit. When the logical level of the zero crossing detector signal is a one, an "up" command is generated at the output of the up/down logic circuit. Conversely, when the logic level of the zero crossing detector signal is a zero, a "down" command is generated. At resonance (i.e. when the transducer pick-up signal lags the excitation signal by 90 degrees), the level of the zero crossing detector signal will alternate between one and zero and therefore generate alternate "up" and "down" signals at the output of up/down logic circuit 37.

These "up" and "down" signals are then input to an 18-bit synchronous up/down counter 41. In the illustrated FIG. 1 embodiment, this counter may, for example, comprise five IC's, such as National model 74HC193. The last 12 stages of this counter provide the preset to the first 12 stages of the 14-bit presettable modulo-N divider, via a 12-bit bus. Counter 41 is also connected to a microprocessor 43.

Resonance is maintained in the circuit through a type of feedback loop from counter 41 to divider 15. The two high order bits of divider 15 are set to one to provide a minimum divisor. This initial preset value causes the divider 15, phase locked loop 17, ROM counter 21, ROM 23 and D/A converter 25 to initially generate a cosine wave at its maximum frequency and to then reduce its frequency as it seeks the resonant point of the density transducer 11. Once the resonant frequency is reached, the up/down logic 37 maintains the preset on the modulo-N counter to maintain the transducer in resonance. The six low order bits of the 18-bit counter 41 act to provide an averaging of sixty-four bits of excitation to the transducer drive coil of density transducer 11 before the value to the preset of the divider 15 is changed. This averaging is required because the ROM counter 21 generates 64 waves before returning an input to the phase locked loop (17) phase input. Any modification to the modulo-N divider 15 would not therefore have an effect on the loop until 64 cycles have occurred.

When resonance has been achieved, data flow at the output of counter 41 is relatively stable, which is sensed by microprocessor 43. Microprocessor 43 may, for example, comprise Hitachi model 6301, and contains programmed instructions within a ROM (not shown) within the microprocessor for conventionally controlling its operation. Achievement of resonance causes the microprocessor to enter a programmed subroutine which reads the value of the preset of the divider 15. This value is directly related to the frequency of transducer excitation at which the coincidence occurred. This value is entered into a polynomial from which the density of the fluid is determined.

The polynomial used to determine density is as follows:

Density (lbs/gal.) $= (Ko + Ka \times T^2)$ where:

Ko, Ka = calibration constants for the transducer; and

T = period of the frequency of excitation, in microseconds.

For aircraft fuel measurement applications, the variable Ko in the above equation may typically be within the range of $-7.515$ to $-5.845$; the variable Ka within the range of 0.0020875 to 0.0029225; and the variable T within the range of 65 usec to 77 usec. Such ranges will permit the measurement of fluid densities over a range of approximately 5 lbs./gal. to 7.5 lbs./gal.

Thus, the period of the excitation frequency at resonance of transducer 11 is extracted from the preset value of the divider 15 and the density of the liquid in which the transducer is immersed is measured. The specific divide ratios are preferably chosen to provide the frequency range required for the particular application. The invention also finds application in various other fields and using various other sensors, such as water, other fluids or air pressure sensors. Such applications may be accomplished by changing the excitation frequency, divide ratios and other variables in an appropriate manner.

The programmed instructions contained in the ROM within microprocessor 43 may be in any suitable form.

Of course, the electronics of the present invention can be applied to transducers other than that described herein, such as for air pressure, where the method of measurement requires an excitation signal to find a resonance point. As should be apparent, modification of certain components, as for example the oscillator or dividers, may be required depending upon the characteristics of the particular transducer.

Figure 2A:
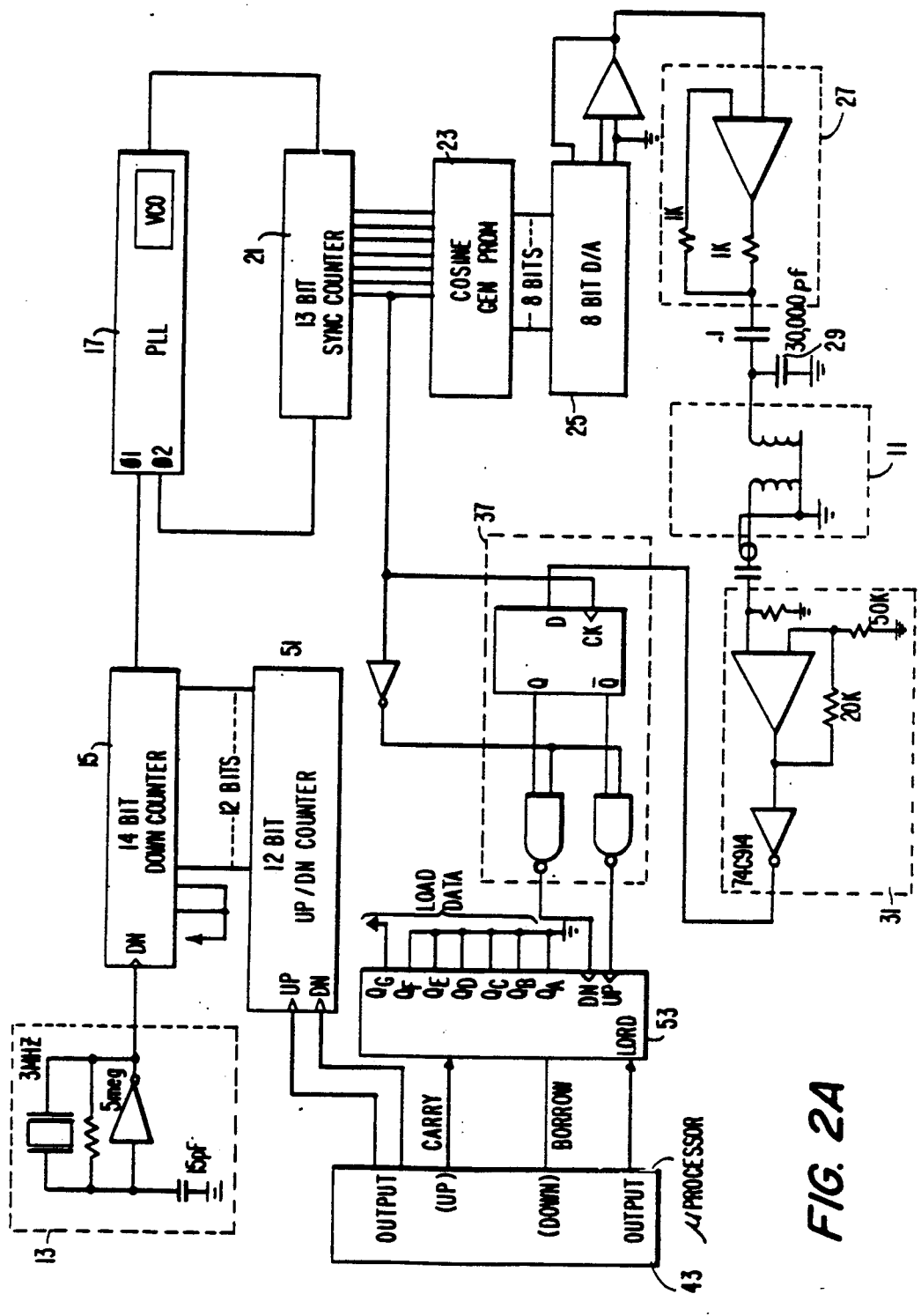
FIG. 2A is a semi-schematic functional block diagram of a second embodiment of the present invention.

FIG. 2A depicts a second embodiment of the invention. The arrangement of FIG. 2A differs from that of FIG. 1 principally in that the 18-bit up-down counter of the first embodiment has been replaced by the combination of a 12-bit synchronous up-down counter 51 and a 7-bit prestage up-down counter 53. The prestage counter 53 is initialized to '64' (binary 0100 0000) and directs its 7-bit output to the microprocessor 43. The microprocessor services—i.e. increments or decrements, as appropriate—the 12-bit up-down counter 51 to change the output of counter 51 and, correspondingly, the divisor of the modulo-N divider 15, in accordance with the output of prestage counter 53.

More particularly, the prestage counter 53 operatively provides an effective delay in incrementing or decrementing counter 51. Each time that the microprocessor 43 services the 12-bit up-down counter 51 it generates a "load" pulse to the prestage counter 53 by which the counter 53 is initialized to a count of '64'. The microprocessor will not again service the 12-bit counter 51 until the prestage counter 53 counts either up to '128' (binary 0111 1111) or down to zero (binary 0000 0000). At that point, however, an "up" or "down" pulse, as appropriate, will be input to the counter 51 by the microprocessor 43 and the prestage counter is reinitialized to '64'. Thus, the prestage counter operates to average or smooth changes in the incrementing and decrementing pulses output from the up/down logic 37; 64 more "up" than "down" pulses—or, conversely, 64 more "down" than "up" pulses—must be input to the prestage counter before the microprocessor will generate a single "up"—or "down"—pulse to the 12-bit counter 51 and, thereby, modify the divisor of modulo-N divider 15. In this manner, the operative stability of the circuit is greatly improved.

Figure 2B:
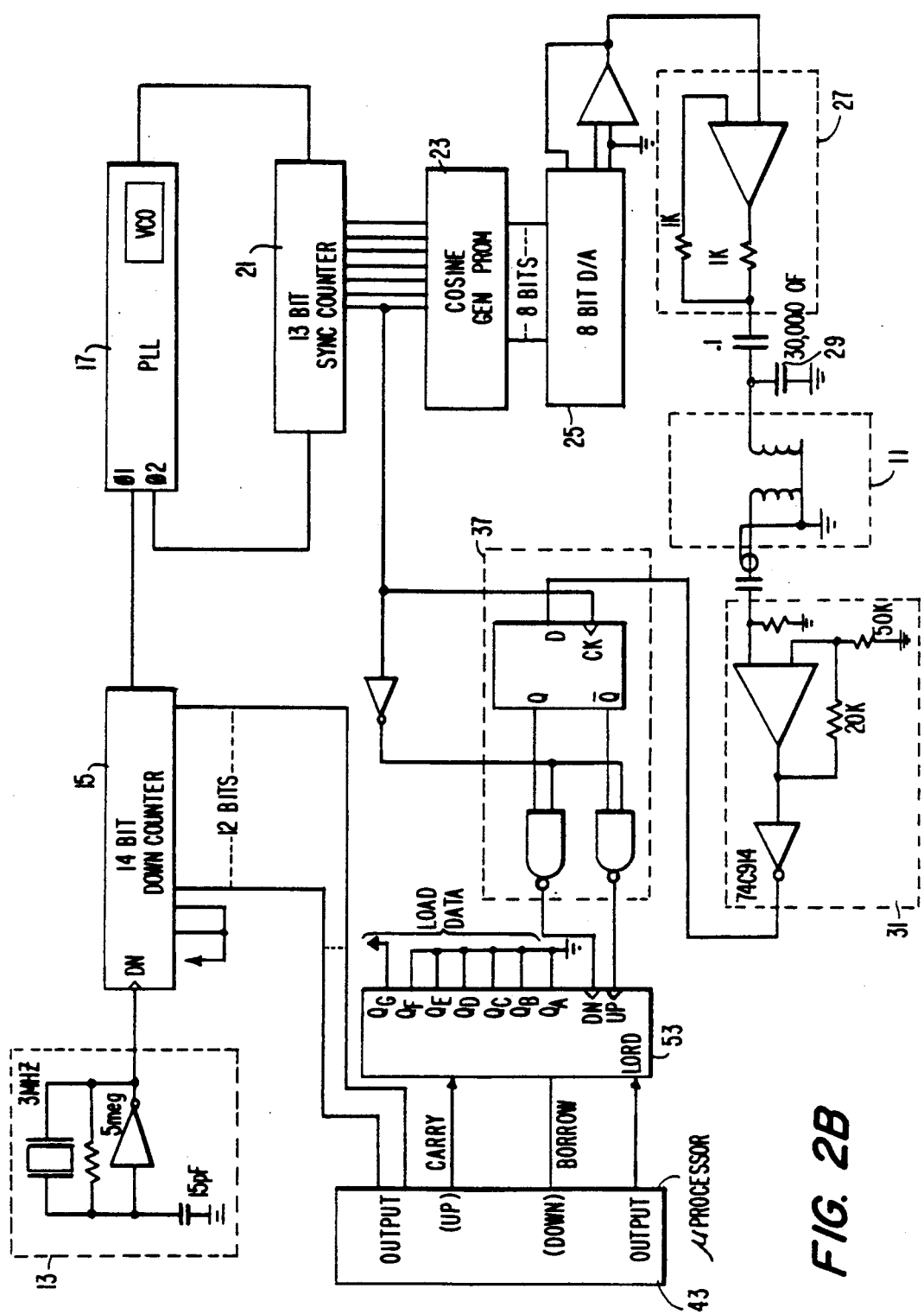
FIG. 2B is a semi-schematic functional block diagram of a third embodiment of the present invention.
Figure 3B:
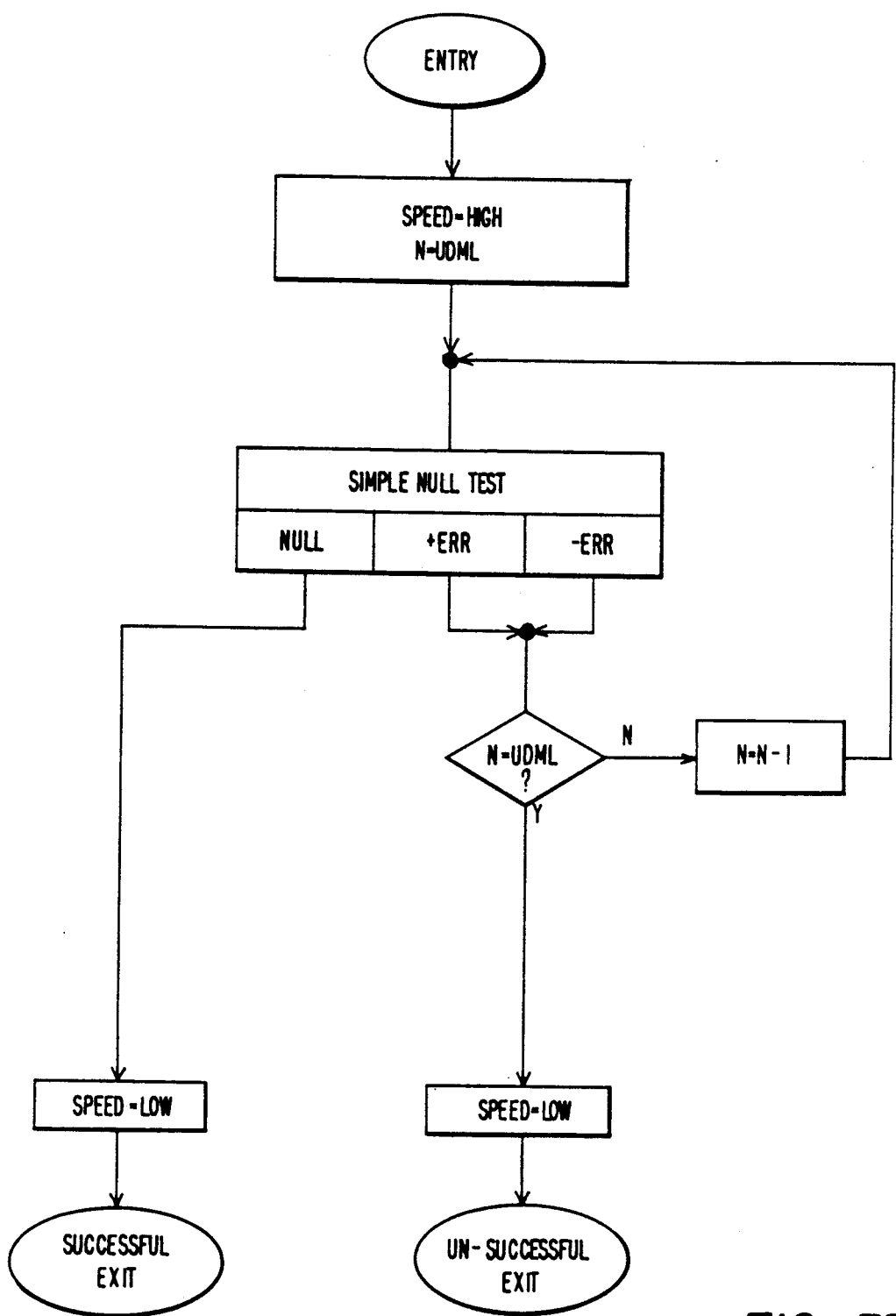
Figure 3C:
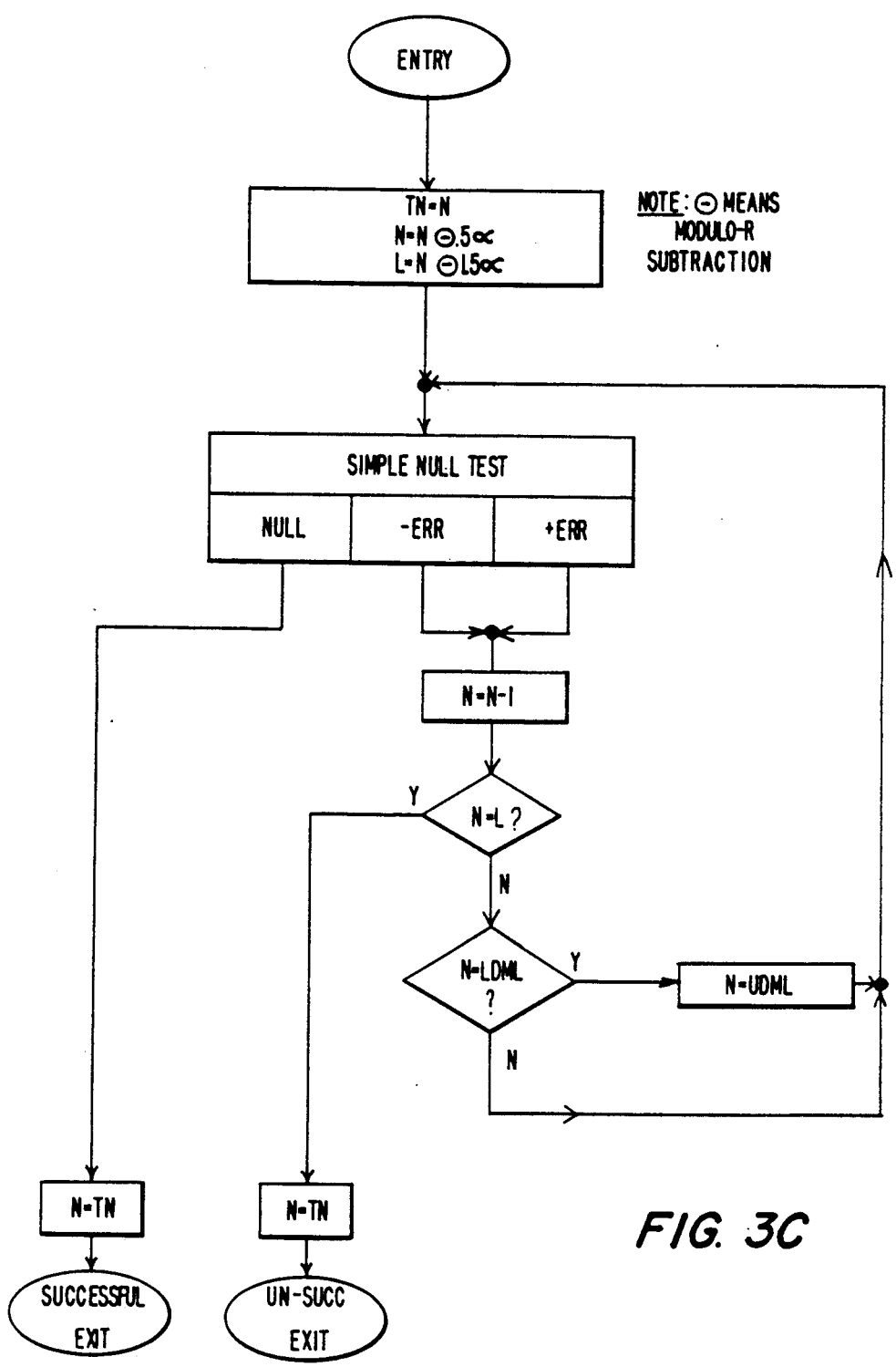
Figure 3D:
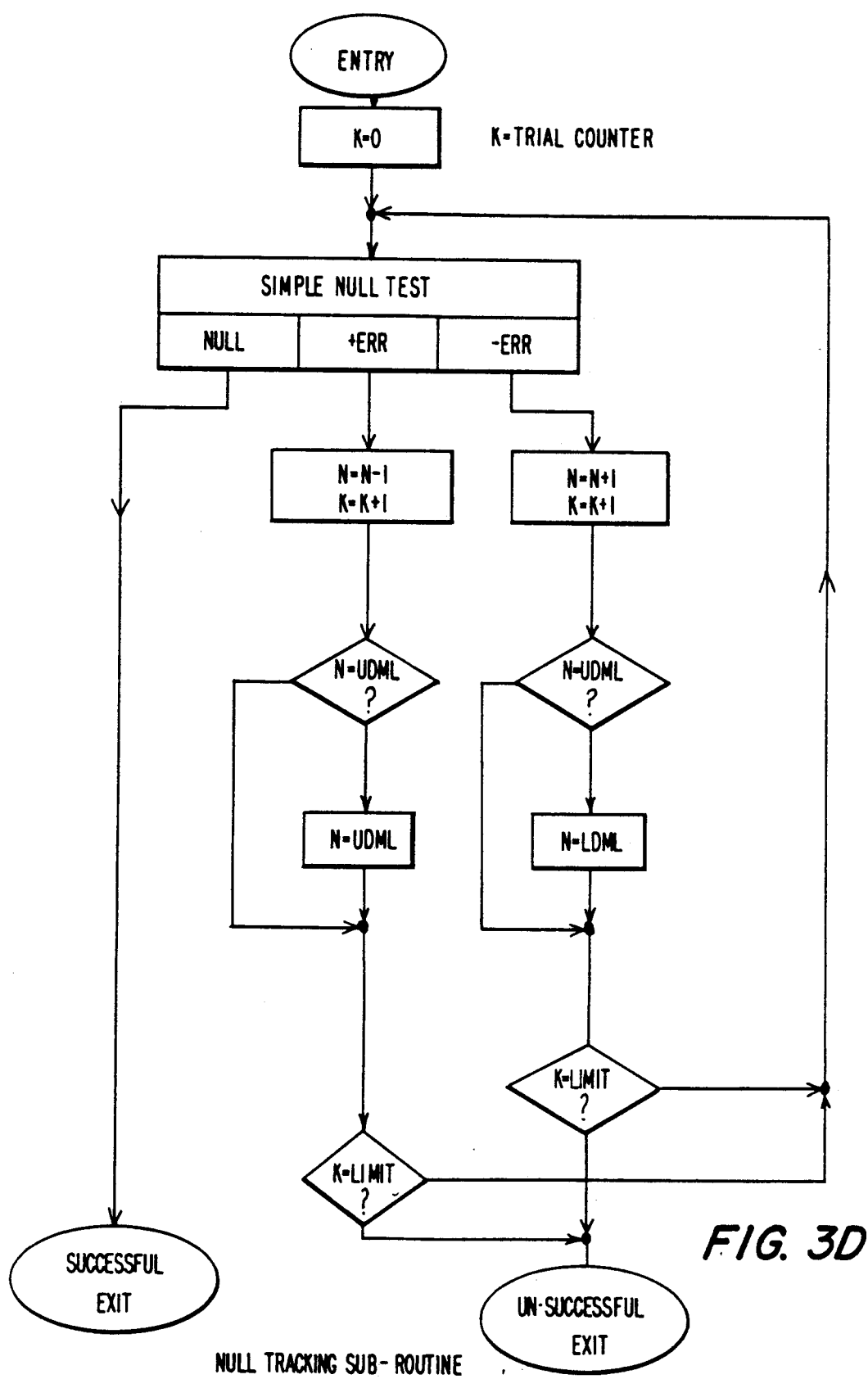
Figure 3E:
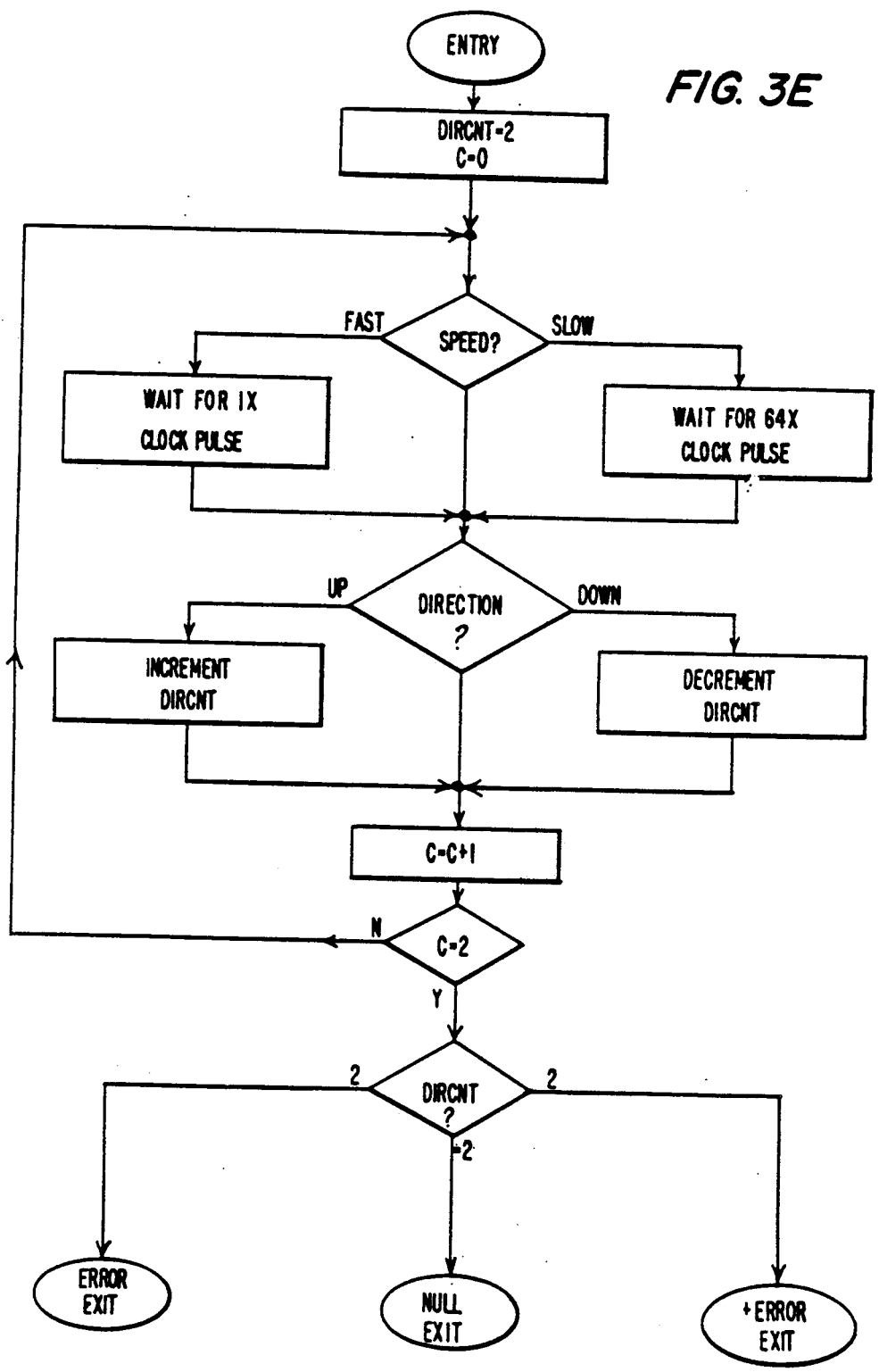

The circuit of FIG. 2B depicts a third and currently most preferred embodiment of the invention. This final embodiment is substantially identical to that of FIG. 2A except that the 12-bit counter 51 of FIG. 2A has been eliminated and, instead, implemented in operating software for the microprocessor 43. In addition, the 7-bit output lines from prestage counter 53 to the microprocessor have been eliminated and replaced by the carry (or overflow) and borrow outputs of the prestage counter for signalling the microprocessor that the 12-bit output to counter 15 should be incremented or decremented, respectively.

FIGS. 3A, 3B, 3C, 3D and 3E are self-explanatory flow charts depicting the operation of the software implementation of the FIG. 2B embodiment. Of course, the software implementation of FIGS. 3A, 3B, 3C, 3D and 3E is disclosed by way of example only, and numerous other implementations may alternatively be employed in accordance with the invention. In any event, the following variable designations are incorporated in the flow charts illustrated in these Figures:

| Variable Name | Description |
| --- | --- |
| 1X Clock | The density transducer's "fast" output. |
| 64X Clock | The density transducer's "slow" output. |
| (alpha) | The mean distance between the True Null and the False Null. |
| C | Loop counter for Simple Null Test routine |
| DIRCNT | Token counter for Simple Null Test routine |
| DIRECTION | The logical sense of the transducer's direction signal. |
| DML | Divider Modulo Limits. |
| LDML | Lower Divider Modulo Limit. |
| K | Trial counter for Null Tracking routine. |
| L | Limit. |
| N | Main up-down counter value |
| R | Range (UDML - LDML). |
| Speed | Linkage flag for Null Test routines. |
| TN | True Null. |
| UDML | Upper Divider Modulo Limit. |

Thus, while there have been shown and described and pointed out fundamental novel features of the invention as applied to preferred embodiments thereof, it will be understood hat various omissions and substitutions and changes in the form and details of the devices illustrated and in their operation may be made by those skilled in the art without departing from the spirit of the invention. It is the intention, therefore, to be limited only as indicated by the scope of the claims appended hereto.

What is claimed is:

1. A densitometer, comprising:
   a density transducer having input means for receiving an excitation signal and output means for generating a phase-varying pick-up signal responsive to the excitation signal and to the density of a fluid in which the density transducer is immersed; and
   excitation and measurement electronics coupled to the density transducer, comprising:
   means for producing an excitation signal of variable frequency and phase for input to the density transducer, said excitation signal comprising a cosine wave, and said excitation signal producing means comprising means for digitally synthesizing a variable frequency cosine wave;
   means for varying the frequency of the excitation signal in response to a variation in phase relationship of the excitation signal and the pick-up signal so as to maintain resonance between the excitation signal and the pick-up signal; and
   means for detecting the phase relationship between the excitation signal and the pick-up signal and for producing an output signal corresponding to the fluid density upon detection of resonance;
   whereby said densitometer is capable of measuring the density of a fluid with a high degree of accuracy despite a substantial physical separation between the density transducer and the excitation and measurement electronics.

2. The densitometer of claim 1 wherein said fluid is liquid aviation fuel, said density transducer being immersed in said liquid aviation fuel, and said densitometer measuring the density of said liquid aviation fuel with a high degree of accuracy.

3. The densitometer of claim 1 wherein the density transducer comprises a vibrating cylinder type transducer.

4. The densitometer of claim 1 wherein the means for producing the excitation signal comprises a pulse train generating means coupled to a read-only memory containing digital cosine wave amplitude information, said read-only memory being coupled to a digital-to-analog converter, and said digital-to-analog converter being coupled to a drive circuit.

5. The densitometer of claim 1 wherein the means for varying the frequency of the excitation signal comprises a feedback loop including a modulo-N divider, where N is responsive to a change in the pick-up signal.

6. The densitometer of claim 1 wherein the means for detecting the phase relationship and producing the output signal includes a programmed microprocessor.

7. The densitometer of claim 5 wherein the feedback loop further comprises a phase locked loop coupled to a read-only memory counter, said read-only memory counter being coupled to a read-only memory, said read-only memory being coupled to a digital-to-analog converter, said digital-to-analog converter being coupled to a zero crossing detector, and said zero crossing detector being coupled to an up/down logic circuit and an up/down counter.

8. The densitometer of claim 7 in which the read-only memory counter operates to produce a digital reference signal for input to the read-only memory, and the read-only memory contains cosine wave amplitude information and operates, in series with the digital-to-analog converter, to generate an analog cosine wave for input to a drive circuit, for generation of the excitation signal.

9. A densitometer, comprising:
   a vibrating cylinder type density transducer, designed for immersion in a liquid, having input means for receiving an excitation signal and output means for generating a pick-up signal responsive to the excitation signal and to the density of the liquid; and
   excitation and measurement electronics coupled to the density transducer, comprising:
   an oscillator for generating a pulse train output;
   a modulo-N divider having two inputs and one output, one said input receiving the pulse train output of the oscillator and the other said input receiving a signal from an up/down counter;

a phase locked loop including a voltage controlled oscillator, having an output coupled to a read-only memory counter and an input coupled to the output of the modulo-N divider, the read-only memory counter having one input and two outputs;

a read-only memory having an input coupled to an output of the read-only memory counter;

a digital-to-analog converter having an input coupled to the output of the read-only memory;

a drive circuit having an input coupled to the output of the digital-to-analog converter, and having an output coupled to the input of the density transducer, the drive circuit being arranged to provide an excitation signal to the density transducer;

a zero crossing detector having an input coupled to the output of the density transducer and arranged to receive said pick-up signal from the density transducer, and having an output coupled to one input of an up/down logic circuit, a second input of the up/down logic circuit being coupled to one of the outputs of the read-only memory counter, the up/down circuit further having two outputs; and an up/down counter having two inputs coupled to the outputs of the up/down logic circuit and having two outputs, one of which outputs is coupled to the input of the modulo-N divider and the other of which outputs is coupled to an input of a programmed microprocessor;

the excitation and measurement electronics serving to provide an excitation signal to the density transducer and to measure the pick-up signal of the density transducer so as to maintain the density transducer in resonance, and to generate a signal corresponding to the frequency of resonance of the density transducer, which signal frequency is indicative of the density of the liquid;

whereby the densitometer is capable of accurately measuring fluid density despite wide physical separation between the density transducer and the excitation and measurement electronics.

* * * * *